United States Patent [19]

Lawrenz et al.

[11] Patent Number: 4,624,149
[45] Date of Patent: Nov. 25, 1986

[54] SAMPLING TUBE

[75] Inventors: Dennis A. Lawrenz, Bridgman; Ken A. Rinkenberg, Stevensville, both of Mich.

[73] Assignee: Leco Corporation, St. Joseph, Mich.

[21] Appl. No.: 702,683

[22] Filed: Feb. 19, 1985

[51] Int. Cl.[4] ............................ G01N 1/12; G01N 1/14
[52] U.S. Cl. ................................. 73/864.52; 73/864.53
[58] Field of Search ......... 73/864.52, 864.53, DIG. 9, 73/864.54, 864.55, 864.56, 864.57, 864.58, 864.59; 249/DIG. 4

[56] References Cited

U.S. PATENT DOCUMENTS

| 2,139,114 | 12/1938 | Demers | 73/864.61 X |
|---|---|---|---|
| 2,143,982 | 1/1939 | Hare et al. | |
| 2,485,492 | 10/1949 | Hubbard et al. | |
| 2,861,450 | 11/1958 | Ransley | 73/19 |
| 2,970,350 | 2/1961 | Feichtinger | |
| 3,315,529 | 4/1967 | Feichtinger | 73/DIG. 9 |
| 3,369,406 | 2/1968 | Lowdermilk et al. | 73/DIG. 9 |
| 3,390,568 | 7/1968 | Taylor | 73/19 |
| 3,452,602 | 7/1969 | Hackett | |
| 3,457,790 | 7/1969 | Hackett | |
| 3,501,963 | 3/1970 | Collins | 73/864.53 |
| 3,534,614 | 10/1970 | Creswell | |
| 3,915,014 | 10/1975 | Judge et al. | 73/864.52 X |
| 3,967,505 | 7/1976 | Feichtinger | 73/DIG. 9 |
| 4,170,139 | 10/1979 | Narita et al. | 73/864.52 |
| 4,428,245 | 1/1984 | Nakamura et al. | 73/864.52 |
| 4,445,390 | 5/1984 | Atwell | 73/864.52 |
| 4,537,747 | 8/1985 | Castaneda | 73/864.52 X |

FOREIGN PATENT DOCUMENTS

| 1922677 | 11/1970 | Fed. Rep. of Germany . | |
| 2035420 | 1/1972 | Fed. Rep. of Germany | 73/DIG. 9 |
| 8648 | 5/1964 | Japan | 73/864.52 |
| 2358 | 1/1978 | Japan | 73/864.52 |
| 2040750 | 9/1980 | United Kingdom | 73/864.52 |
| 623130 | 8/1978 | U.S.S.R. | 73/864.53 |

Primary Examiner—Stewart J. Levy
Assistant Examiner—Tom Noland
Attorney, Agent, or Firm—Price, Heneveld, Huizenga & Cooper

[57] ABSTRACT

A sampling tube includes a sealed metallic tube having a fusible end cap at an extending end which, when submerged in a molten bath, admits the molten sample into the evacuated tube. The tube has a liner which is either frangible or has a nonadhering surface defining a substantially uniform, cross-sectional diameter to freely allow the molten sample to enter the tube and solidify in the liner as the sample tube is removed.

17 Claims, 5 Drawing Figures

SAMPLING TUBE

BACKGROUND OF THE INVENTION

The present invention relates to a sampling tube for obtaining molten metal samples.

In the determination of the content of the molten metal, such as during steel manufacturing process, it is desirable to monitor the content of the melt during various stages of production. A variety of sampling devices have been suggested, particularly for use with specimen gases such as hydrogen, which is particularly difficult to sample and determine inasmuch as gaseous hydrogen can easily escape while residual hydrogen remains in the solid specimen removed by the sampling device. U.S. Pat. No. 4,445,390 discloses a sampling device for the removal of a sample from a molten metal bath to capture the total hydrogen content of a sample. In this and other evacuated tube samplers, however, the molten metal bonds to the wall surfaces of the sampler, and when the solid sample is analyzed therefore, the resultant pin sample includes not only the molten metal desired to be sampled but a section of the sampling device itself. Although the weight and impurities, if any, in the sampling tube can be compensated for, by estimation, but the results are not as accurate as obtainable with the sampling device of the present invention which allows the actual weight of the pin sample to be determined.

SUMMARY OF THE PRESENT INVENTION

The sampling tube of the present invention is an improvement over the above identified sampling tube and includes a sealed metallic tube having a fusible end cap at an extending end which, when submerged in a molten bath, admits the molten sample into the evacuated tube. The tube has a liner which is either frangible or has a nonadhering surface defining a substantially uniform, cross-sectional diameter to freely allow the molten sample to enter the tube and solidify in the liner as the sample tube is removed.

The sample tube is pierced at spaced locations along its axis for the removal of gas samples therefrom for analysis. Once, for example, the diffusible hydrogen has been removed and analyzed, the tube can be broken or cut to provide access to the solid pin sample obtained which is easily removed from the tube by removing the liner, or if a frangible liner is employed, by breaking the liner for subsequent weight determination of the pin and analysis of the residual hydrogen contained in the pin.

These and other features, advantages and objects of the present invention will become apparent to those skilled in the art upon reading the following description thereof together with reference to the drawing figures in which:

DETAILED DESCRIPTION OF THE PREFERRED EMBODIMENT

Figure 1:
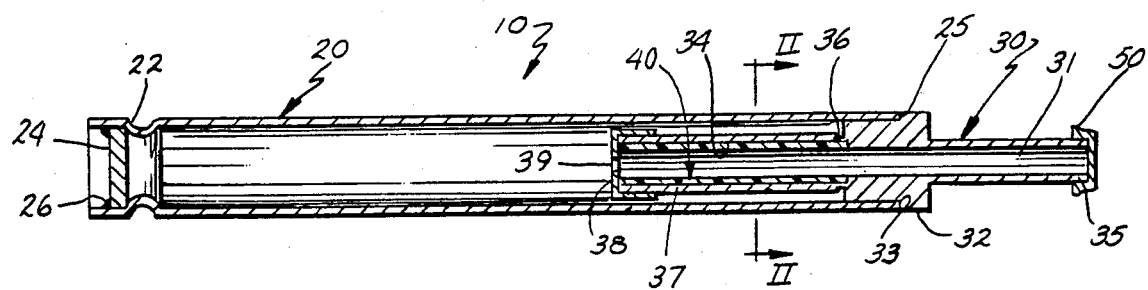
FIG. 1 is a vertical, cross-sectional view of the sampling tube embodying the present invention.
Figure 2:
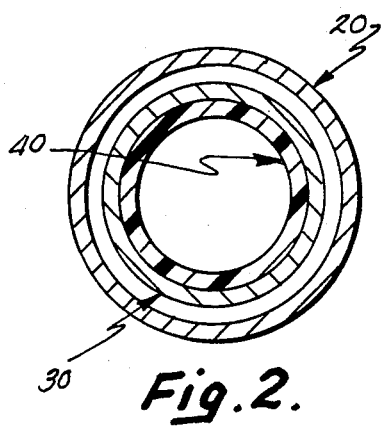
FIG. 2 is an enlarged, cross-sectional view taken along section line II—II of FIG. 1.
Figure 3:
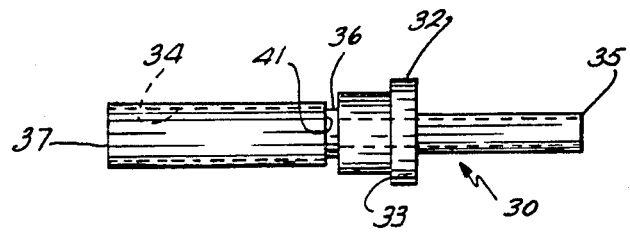
FIG. 3 is a side elevational view of a portion of the tube shown in FIG. 1.

Referring initially to FIGS. 1 and 2, sampling tube 10 includes a circular-cylindrical outer tube 20 which sealably encloses one end of an inner or sample tube 30. Tube 30 extends partially within tube 20 and coaxially mounted thereto. The steel outer tube has an overall length, in the preferred embodiment, of approximately 4.75 inches, an outer diameter of approximately 0.5 inches and an inner diameter of approximately 0.46 inches. Near one end of tube 20, there is an annular roll-formed depression 22 defining a stop for a disc-shaped end cap 24 inserted in the end and brazed around its periphery, as indicated by bead 26, to sealably enclose this end of tube 20 during the manufacturing process. The opposite end 25 of tube 20 is initially open to receive coaxially fitted inner tube 30. Steel tube 30 is also circular-cylindrical and has an overall length of approximately 2.81 inches and an integrally machined annular collar extending from a first end 35 a distance of approximately 1 inch. Collar 32 has a rearward facing annular surface 33 defining a seat for the end 25 of tube 30 which junction is sealed by a brazing bead during assembly.

Tube 30 includes an outer annular recess 36 formed approximately 0.3 inches behind collar 32 to define a breaking point for snapping off the smaller diameter end 37 of tube 30 remote from end 35. End 37 includes a liner 40, as described below, and defines, in effect, a mold for forming a solid pin sample during use. The outwardly projecting end 35 of tube 30 has an inner diameter of about 0.2 inches while the opposite end 37 is counterbored to define an elongated, internal, annular recess 34 with a diameter of about 0.29 inches extending inwardly from end 37 about 1.36 inches.

Figure 4:
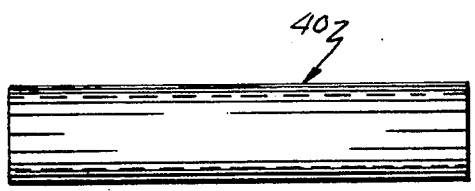
FIG. 4 is a side elevational view of the tube liner also shown in FIGS. 1 and 2.
Figure 5:
FIG. 5 is a right side elevational view of the structure shown in FIG. 4.

Fitted within recess 34 is a liner 40 (FIGS. 1, 4 and 5) comprising a 7 mm outer diameter quartz glass cylindrical tube in the preferred embodiment having an inner diameter of 5 mm and a length of 1.35 inches. An important property of liner 40 is that the molten metal sample will not stick to the interior cylindrical surface thereof as it cools thereby preventing any bonding between the pin sample and the sample tube 30 as with prior art samplers. The liner, therefore, can be made of a material to which the molten metal will not adhere during cooling such that the pin can be pushed from the snapped off end 37 of the tube 30 for subsequent analysis of residual material contained in the pin, or the material can be frangible such that the liner can be broken for removal of the pin. Some material for the liner will display both desired properties. The quartz tube employed in the preferred embodiment has a coefficient of expansion different than that of the molten metal obtained from a bath having a temperature of from 2,800° F. to 3,000° F., and therefore, frequently, the molten metal sample will shrink and be free of the liner upon solidification as it cools. If some sticking does occur, however, the liner is frangible allowing the liner to be broken away from the pin. The pin or the pin and liner are removed axially from the end 37 or 41 of the inner tube by use of a push rod or the like. The liner has an inner diameter which corresponds to the inner diameter of end 35 of the inner sampling tube such that a smooth, continuous flow path for the liquid molten metal entering end 35 into the inner sampling tube is provided.

End 35 of the tube 30 includes a fusible end cap 50 brazed thereon and made of stainless steel having a thickness of about 0.005 inches and which melts when the sample is immersed in a molten metal bath. At the opposite end of tube 30, there is provided a closure cap 38 (FIG. 1) with a cylindrical flange which is press-fit over the end 37 of tube 30 and includes a central aperture 39 having a diameter of approximately 0.020 inches. Aperture 39 admits gas which escapes from the molten metal sample into the body of the sampling device 10.

Each of the tubes 20 and 30 are made of a suitable material such as steel with the outer diameter of tube 30 and cap 38 slightly less than the inner diameter of tube 20 to permit ready assembly of the two tubes during manufacturing. During assembly, liner 40 is inserted into the recess 34 through open end 37 of the tube 30. Cap 38 is then fitted over the end 37 of tube 30, cap 50 fitted over end 35 of tube 30 and the tubes physically positioned together. Cap 24 is then placed on stop 22, and the structure placed in a suitable vacuum furnace to evacuate the tube to approximately $10^{-4}$ mm and caps 24 and 50 and collar 32 brazed in place using brazing rings appropriately positioned during assembly. Thus, the assembly is evacuated during manufacturing to provide a negative pressure sealed unit.

Tube 10 is then inserted into a cardboard sleeve and partially surrounded by an insulating material with end 35 exposed a distance of approximately 0.625 inches for immersion into a metal bath for withdrawing of a molten metal sample. As the sample is taken, cap 50 melts, allowing admission of the molten metal into tube 30 along uniform cylindrical passageway 31 which includes the inner cylindrical wall of the liner 40. Diffusible hydrogen released by the molten metal as it cools flows through aperture 39 in cap 38 into the volume defined by the inner cylindrical space of outer tube 20 and is sealably contained therein. The molten metal sample solidifies as the sampling tube is removed from the molten bath to seal end 35 of cylindrical bore 31 to effectively trap the diffusible hydrogen within tube 20 and the solid metal sample within tube 30 with the particular pin sample being located within the liner area 40 of tube 30.

In order to remove the diffusible or free hydrogen from sampling tube 10 for analysis, the automatic tube piercing apparatus disclosed in U.S. Pat. No. 4,445,390 can be employed. A detailed description of this apparatus and the flow diagram for removal of diffusible hydrogen is provided in the above identified patent, the disclosure of which is incorporated herein by reference. This device couples to an analyzer such as a Model DH-102 or DH-103 hydrogen analyzer available from Leco Corporation of St. Joseph, Mich., for the measurement of the hydrogen concentration. Once the diffusible hydrogen is measured by the analyzer, as noted above, the sampling device 10 is cut open such that the end 37 of inner tube 30 can be snapped off at recess 36 allowing the cylindrical metal pin captured within liner 40 to be removed by ejection along the longitudinal axis of the tube 30, exiting from the broken off end 41. By employing a liner to which the pin sample does not stick, the pins will either drop out relatively easily or can be relatively easily ejected. If a frangible liner is employed, the liner can be broken to facilitate removal of the pin.

Although sampling device 10 is particularly suitable for use in the determination of total hydrogen content of a molten metal bath, the device can be used for the capturing of a molten metal sample for analysis of other elements. Although quartz is the preferred liner material, ceramic or other material may be used if they display the desired properties.

It will become apparent to those skilled in the art that various modifications to the preferred embodiment of the invention can be made without departing from the spirit or scope thereof as defined by the appended claims.

The embodiments of the invention in which an exclusive property or privilege is claimed are defined as follows:

1. A molten metal immersion sampling device comprising:
   an evacuated cylindrical metallic tube sealably enclosed at one end and having a sample receiving opposite end sealed by a fusible material, a frangible liner positioned within said tube in coaxial relationship therewith and spaced inwardly from said opposite end of said tube, said liner extending along at least a portion of the interior of said tube and having one end for receiving a molten sample and an opposite end enclosed to prevent escape of molten metal therethrough, said liner defining a pin sample mold for allowing easy removal of a pin sample from said metal tube, said metal tube conducting heat away from said one end of said liner to solidify the molten sample adjacent said one end of said liner to form a seal to prevent the loss of diffusible gases from said tube upon removal of said tube from the molten metal bath.

2. The sampling device as defined in claim 1 wherein said liner is made of quartz.

3. The sampling device as defined in claim 2 wherein said liner is cylindrical.

4. The sampling device as defined in claim 2 wherein said tube includes an internal annular recess for seating said liner therein.

5. The sampling device as defined in claim 4 wherein said liner extends along only a portion of said tube and the inner diameter of said liner is substantially the same as the inner diameter of said tube.

6. A molten metal immersion sampling device comprising:
   a cylindrical evacuated metallic tube sealably enclosed at one end and having a sample receiving opposite end sealed by a fusible material, said tube including a liner positioned within said tube and spaced inwardly from said opposite end of said tube, said liner made of a material to which a molten sample will not permanently adhere, said liner extending along at least a portion of said tube to define a pin sample mold for allowing easy removal of a pin sample from said metal tube; and
   metallic collar means having a thickness greater than the thickness of said sample receiving end of said tube, said collar means positioned adjacent an end of said liner proximate said sample receiving opposite end of said metallic tube.

7. The sampling device as defined in claim 6 wherein said liner is made of frangible material.

8. The sampling device as defined in claim 7 wherein said liner is cylindrical and made of quartz.

9. The sampling device as defined in claim 8 wherein said collar is integrally formed with said tube.

10. The sampling device as defined in claim 9 wherein said tube includes an internal annular recess for seating said liner therein.

11. The sampling device as defined in claim 10 wherein said liner extends along only a portion of said tube and the inner diameter of said liner is substantially the same as the inner diameter of said tube.

12. A molten metal sampling device comprising:
an outer cylindrical tube sealably enclosed at one end and open at an opposite end;
a cylindrical inner tube coaxially and sealably fitted at least partially within said opposite end of said outer tube and having an extending end sealed with a fusible material and an opposite end positioned within said outer tube and including closure means for blocking the flow of molten metal into said outer tube while permitting the flow of gas therein, said inner tube including an annular inner recess for receiving a liner and a collar at the junction of said inner and outer tubes, said collar having a thickness greater than that of said extending end; and
a cylindrical liner coaxially positioned within said inner tube, said liner having one end adjacent said collar and extending along said annular inner recess for forming a pin sample within said liner.

13. The apparatus as defined in claim 12 wherein said liner is made of a frangible material.

14. The apparatus as defined in claim 12 wherein said liner is made of quartz.

15. A molten metal sampling device comprising:
an outer cylindrical metal tube sealably enclosed at one end and open at an opposite end;
a metal cylindrical inner tube coaxially and sealably fitted at least partially within said opposite end of said outer tube and having an extending end sealed with a fusible material and an opposite end positioned within said outer tube and including means for blocking the flow of molten metal into said outer tube, said inner tube including an internal annular recess for receiving a frangible cylindrical liner, said liner extending in coaxial alignment with said inner, tube and surrounded thereby, said inner tube further including a collar section of increased thickness adjacent one end of said liner whereby molten metal entering said extending end solidifies to seal said inner tube to prevent the loss of diffusible gases from said tube upon removal of said tube from a molten metal bath.

16. The apparatus as defined in claim 15 wherein said tube is evacuated.

17. The apparatus as defined in claim 16 wherein said liner is made of quartz.

* * * * *